(12) United States Patent
Mason

(10) Patent No.: US 7,309,333 B2
(45) Date of Patent: Dec. 18, 2007

(54) MEDICATION DELIVERY SYSTEM HAVING SELECTIVE AUTOMATED OR MANUAL DISCHARGE

(75) Inventor: Jeffrey T. Mason, Escondido, CA (US)

(73) Assignee: Breg, Inc., Vista, CA (US)

( * ) Notice: Subject to any disclaimer, the term of this patent is extended or adjusted under 35 U.S.C. 154(b) by 339 days.

(21) Appl. No.: 10/933,619

(22) Filed: Sep. 2, 2004

(65) Prior Publication Data

US 2005/0033262 A1 Feb. 10, 2005

Related U.S. Application Data

(62) Division of application No. 09/935,392, filed on Aug. 22, 2001, now Pat. No. 6,802,823.

(51) Int. Cl.
*A61M 31/00* (2006.01)
(52) U.S. Cl. .................. 604/500; 604/131; 604/135; 604/251
(58) Field of Classification Search ............... 604/500, 604/51, 135
See application file for complete search history.

(56) References Cited

U.S. PATENT DOCUMENTS

| 523,345 | A | 7/1894 | Hardman, Jr. |
| 788,176 | A | 4/1905 | Traves |
| 1,493,592 | A | 5/1924 | Beck |
| 1,847,954 | A | 3/1932 | Fisher |
| 2,044,911 | A | 6/1936 | Miller ............... 128/227 |
| 2,183,482 | A | 12/1939 | Kurkjian ............... 128/261 |
| 2,471,623 | A | 5/1949 | Hubbel ............... 251/5 |
| 3,003,500 | A | 10/1961 | Barton et al. ............... 128/214 |
| 3,598,119 | A | 8/1971 | White ............... 128/215 |
| 3,854,477 | A | 12/1974 | Smith ............... 128/213 |
| 4,038,983 | A * | 8/1977 | Mittleman et al. ............ 604/124 |
| 4,337,770 | A | 7/1982 | Young et al. ............ 128/214 R |
| 4,381,006 | A | 4/1983 | Genese ............ 128/218 |
| 4,381,591 | A | 5/1983 | Barger et al. ............ 29/157.1 R |
| 4,498,904 | A | 2/1985 | Turner et al. ............... 604/211 |
| 4,597,754 | A | 7/1986 | Thill et al. ............... 604/154 |
| 4,623,330 | A | 11/1986 | Laby et al. ............... 604/63 |
| 4,685,912 | A * | 8/1987 | Jones ............... 604/247 |

(Continued)

*Primary Examiner*—Kevin C. Sirmons
*Assistant Examiner*—Phillip Gray
(74) *Attorney, Agent, or Firm*—Rodney F. Brown

(57) ABSTRACT

A portable medication delivery system enables a patient to elect slow continuous auto-administration or rapid bolus self-administration of a fluid medication. The medication delivery system has an infusion pump, which includes a fluid storage chamber and a spring-driven piston positioned in the fluid storage chamber. The fluid storage chamber is initially charged with the medication and the infusion pump automatically delivers a continuous dosage of the medication at a first flow rate over a long time from the fluid storage chamber to a treatment site in the patient. A bolus injector is positioned in series or in parallel with the infusion pump and is charged with a bolus dosage of the treatment fluid from the fluid storage chamber for alternate manual self-injection of the medication into the treatment site at a higher second flow rate for a short time. The infusion pump flowpath includes a drip chamber having an in-line flow restriction, which converts a continuous flow stream from the fluid storage chamber to a drip stream. A sight window in the drip chamber permits the user to visually confirm the flow of medication through the infusion pump.

18 Claims, 6 Drawing Sheets

U.S. PATENT DOCUMENTS

| | | | |
|---|---|---|---|
| 4,813,926 A | 3/1989 | Kerwin | 604/118 |
| 4,813,937 A | 3/1989 | Vaillancourt | 604/131 |
| 4,857,059 A | 8/1989 | Rey et al. | 604/185 |
| 4,863,428 A | 9/1989 | Chevalier | 604/130 |
| 4,863,429 A | 9/1989 | Baldwin | 604/135 |
| 4,874,386 A | 10/1989 | O'Boyle | 604/246 |
| 4,921,487 A | 5/1990 | Buffet et al. | 609/135 |
| 4,966,585 A | 10/1990 | Gangemi | 604/131 |
| 4,991,742 A | 2/1991 | Chang | 222/95 |
| 4,997,420 A | 3/1991 | LeFevre | 604/121 |
| 5,011,477 A | 4/1991 | Winchell et al. | 604/132 |
| 5,061,243 A | 10/1991 | Winchell et al. | 604/132 |
| 5,069,668 A | 12/1991 | Boydman | 604/121 |
| 5,084,021 A | 1/1992 | Baldwin | 604/131 |
| 5,100,389 A | 3/1992 | Vaillancourt | 604/135 |
| 5,106,376 A | 4/1992 | Mononen et al. | 604/164 |
| 5,318,539 A | 6/1994 | O'Neil | 604/118 |
| RE35,192 E * | 3/1996 | Reese | 604/512 |
| 5,505,707 A | 4/1996 | Manzie et al. | 604/131 |
| 6,159,188 A | 12/2000 | Laibovitz et al. | 604/289 |
| 6,247,995 B1 | 6/2001 | Bryan | 124/74 |
| 6,735,701 B1 | 5/2004 | Jacobson | |

* cited by examiner

MEDICATION DELIVERY SYSTEM HAVING SELECTIVE AUTOMATED OR MANUAL DISCHARGE

This a divisional application of Ser. No. 09/935,392 filed on Aug. 22, 2001 now U.S. Pat. No. 6,802,823.

TECHNICAL FIELD

The present invention relates generally to a system for delivering medicine to a patient, and more particularly, to a system having in combination a spring-driven infusion pump and a bolus injector, which enable a user to selectively deliver a predetermined dosage of a fluid medication to a treatment site either automatically at a moderate flow rate over a long time or manually at a higher flow rate over a short time.

BACKGROUND OF THE INVENTION

Pain management is an important aspect of post-operative recovery from surgery. Pain management usually begins immediately following the surgical procedure with the administration of narcotics or other pain control medications to the patient while the patient is under the direct supervision of the health care provider. The pain control medications are most commonly administered either orally or by injection.

The proliferation of less-invasive arthroscopic techniques for the surgical repair of many joint or soft tissue injuries and ailments has significantly reduced post-operative recovery times and the attendant pain experienced by the patient. The current trend toward arthroscopic techniques frequently enables surgical procedures to be performed on an outpatient basis or with shortened post-operative hospital stays. As a result, the bulk of the post-operative recovery time is spent in the home or even in the workplace. One goal of home recovery is to phase the patient back into routine physical activities relatively quickly as a means of shortening the post-operative recovery time.

Since the patient is generally not under the direct supervision of the health care provider when in the home or workplace, the responsibility for administering pain control medications falls on the patient in these environments. The vast majority of self-administered pain control medications are oral medications because most individuals lack the requisite knowledge, skill, and experience to self-administer pain control medications by injection. Unfortunately, however, pain control medications administered orally are transported throughout the body and correspondingly affect the entire body, often causing undesirable side effects such as drowsiness, disorientation, nausea, constipation or vomiting. In contrast, injected pain control medications can be administered more locally than orally administered medications, thereby frequently avoiding the undesirable side effects of oral medications. In addition, injected pain control medications reach the treatment site more rapidly and in greater concentrations than oral medications, rendering injected pain control medications a more effective pain control therapy.

To exploit the advantages of injected pain care medications, devices have been developed to inject the pain care medication into the treatment site in an automated manner, which requires minimal patient intervention. Such devices typically meter the pain care medication to the treatment site continuously over a long period of time. Automated continuous injection devices are, nevertheless, not entirely satisfactory. It has been found in many instances that pain care medication is most effective if periodically injected into the treatment site as a single relatively large bolus dosage whenever the patient senses the need rather than continuously injecting the same overall dosage of medication into the treatment site over a relatively long period of time. However, if the patient is allowed to self-administer injection of the pain care medication on an as needed basis in the absence of supervision of a health care provider, the risk of overmedication is significant.

The present invention recognizes a need for a fluid injection device, which selectively enables effective auto-administration of a fluid medication or, in the alternative, effective self-administration of the fluid medication by a patient while diminishing the risk of overmedication, even when the patient lacks the requisite knowledge, skill or experience to perform injections. Accordingly, it is an object of the present invention to provide a medication delivery system, wherein operation of the system is selective between an automated or extended mode and a manual or instantaneous mode. More particularly, it is an object of the present invention to provide such a medication delivery system, wherein the patient elects extended injection of a predetermined dosage of a fluid medication into a treatment site at a moderate flow rate over a long time or, in the alternative, elects to effect instantaneous injection of the predetermined dosage of the fluid medication into the treatment site at a higher flow rate over a short time. It is another object of the present invention to provide such a medication delivery system, wherein the system can effectively reduce the risk of overmedication even when the patient operates the system in the manual or instantaneous mode. It is still another object of the present invention to provide such a medication delivery system, wherein the system can be effectively monitored and operated by a patient lacking any specific medical knowledge, skill or experience in performing injections. It is yet another object of the present invention to provide such a medication delivery system, which is fully portable while operating so that the system can be used by the patient during normal daily activity.

These objects and others are accomplished in accordance with the invention described hereafter.

SUMMARY OF THE INVENTION

A first embodiment of the present invention is a medical infusion pump comprising a fluid storage chamber, a pump outlet, and a pump flowpath positioned between the fluid storage chamber and the pump outlet to provide fluid communication therebetween. The pump flowpath includes a flow restriction, a drip chamber, an outlet tube and a sight window. The flow restriction exits into the drip chamber and the sight window is oriented to enable visual contact with the drip chamber. The flow restriction is sized to convert a continuous stream of fluid entering the flow restriction from the fluid storage chamber to a drip stream exiting the flow restriction into the drip chamber. The outlet tube is positioned beneath the flow restriction in the drip chamber and separated from the flow restriction by a drip gap. The outlet tube is configured to revert the drip stream exiting the flow restriction to a reverted continuous stream. The infusion pump further comprises a displacement piston displacably positioned in the fluid storage chamber and an elastic member engaging the displacement piston and transitionable between a more stressed position and a less stressed position to displace the displacement piston. The elastic member is preferably a coil spring.

Another embodiment of the present invention is a medication delivery system comprising an infusion pump and a bolus injector. The infusion pump includes a fluid storage chamber, a pump outlet, a pump flowpath providing fluid communication between the fluid storage chamber and the pump outlet, a displacement piston displacably positioned in the fluid storage chamber, and an elastic member engaging the displacement piston and transitionable between a more stressed position and a less stressed position to displace the displacement piston. The bolus injector is positioned in series with the infusion pump and is a flexible bladder enclosing a bolus chamber. The bolus chamber has a fluid capacity substantially less than the fluid storage chamber. The bladder may have an elastic memory to restore the bladder to an initial configuration after the bladder is deformed by compression. The bolus injector has an injector inlet into the bolus chamber and an injector outlet out of the bolus chamber. The injector inlet is connected to the pump outlet. The pump flowpath may include a flow restriction, drip chamber, outlet tube and sight window substantially as recited above.

A further embodiment of the present invention is a medication delivery system comprising a first infusion pump, a second infusion pump, a bolus injector, a junction and a common flow tube. The first infusion pump includes a first fluid storage chamber, a first pump outlet, a first pump flowpath providing fluid communication between the first fluid storage chamber and the first pump outlet, a first displacement piston displacably positioned in the first fluid storage chamber, and a first elastic member engaging the first displacement piston and transitionable between a more stressed position and a less stressed position to displace the first displacement piston. The second infusion pump similarly includes a second fluid storage chamber, a second pump outlet, a second pump flowpath providing fluid communication between the second fluid storage chamber and the second pump outlet, a second displacement piston displacably positioned in the second fluid storage chamber, and a second elastic member engaging the second displacement piston and transitionable between a more stressed position and a less stressed position to displace the second displacement piston. The bolus injector is positioned in series with the second infusion pump and is substantially as recited above. The second pump outlet is connected to the injector inlet and the junction connects the first pump outlet with the injector outlet. The common flow tube exits the junction and is in fluid communication with the first pump outlet and the injector outlet. The first pump flowpath may include a flow restriction, drip chamber, outlet tube and sight window substantially as recited above.

Yet another embodiment of the present invention is a medication delivery system comprising an infusion pump, a bolus injector, a junction and a common flow tube. The infusion pump includes a fluid storage chamber, a first pump outlet and a second pump outlet, a pump flowpath providing fluid communication between the fluid storage chamber and the first pump outlet, a displacement piston displacably positioned in the fluid storage chamber, and a elastic member engaging the displacement piston and transitionable between a more stressed position and a less stressed position to displace the displacement piston. The bolus injector is substantially as recited above. The second pump outlet is connected to the injector inlet and the junction connects the first pump outlet with the injector outlet. The common flow tube exits the junction and is in fluid communication with the first pump outlet and the injector outlet. The first pump flowpath may include a flow restriction, drip chamber, outlet tube and sight window substantially as recited above.

Still another embodiment of the present invention is a method for delivering a fluid medication to a treatment site of a patient. A bolus injector is charged with a fluid medication. The bolus injector is a flexible bladder enclosing a bolus chamber and having an injector inlet into the bolus chamber and an injector outlet out of the bolus chamber. A fluid storage chamber serially positioned upstream of the bolus injector is also charged with the fluid medication. The fluid storage chamber is in fluid communication with a pump outlet via a pump flowpath and the pump outlet is in fluid communication with the injector inlet. A displacement force is applied to the fluid medication in the fluid storage chamber from an elastic member transitioning from a more stressed position to a less stressed position. The displacement force serially displaces the fluid medication from the fluid storage chamber and the pump flowpath into the bolus chamber. An outlet valve positioned at the injector outlet, which is biased closed is opened in response to the ambient pressure of the fluid medication contacting the outlet valve to discharge the fluid medication from the injector outlet. The method may further comprise connecting the injector outlet with an inlet end of a catheter, positioning an outlet end of the catheter in a treatment site of a patient, and displacing the fluid medication through the catheter to deliver the fluid medication to the treatment site.

In accordance with specific aspects of the present embodiment, the bolus injector is charged with the fluid medication by displacing the fluid medication from the pump flowpath into the bolus chamber. Alternatively, the bolus injector is charged with the fluid medication by injecting the fluid medication into the bolus chamber from a source downstream of the infusion pump. In accordance with another specific aspect of the present invention, the fluid medication is preferably displaced from the fluid storage chamber as a continuous stream. The continuous stream of the fluid medication is then driven into a flow restriction in the pump flowpath and the fluid medication exits the flow restriction as a drip stream.

Another embodiment of the present invention is a method for delivering a fluid medication to a treatment site of a patient, which comprises charging a bolus injector and a fluid storage chamber serially positioned upstream of the bolus injector with a fluid medication substantially as described above. The practitioner then selects between an extended mode and an instantaneous mode of delivering the fluid medication to a treatment site. The extended mode is performed by applying a first displacement force to the fluid medication in the fluid storage chamber from an elastic member transitioning from a more stressed position to a less stressed position. The first displacement force serially displaces the fluid medication from the fluid storage chamber through the pump flowpath, the bolus chamber and the injector outlet into the treatment site at a first flow rate over a long time. The instantaneous mode is performed by applying a second displacement force to the bolus injector sufficient to deform the bolus injector. The second displacement force displaces the fluid medication from the bolus chamber and discharges the fluid medication from the injector outlet into the treatment site at a higher second flow rate over a short time. The method further comprises recharging the bolus injector with the fluid medication after the instantaneous mode of operation by applying the first displacement force to the fluid medication in the fluid storage chamber. The first displacement force serially displaces the fluid medication from the fluid storage chamber through the pump flowpath and injector inlet into the bolus chamber.

In accordance with a specific aspect of the present embodiment, the fluid medication is preferably displaced from the fluid storage chamber as a continuous stream. The continuous stream of the fluid medication is driven into a flow restriction in the pump flowpath and the fluid medication exits the flow restriction as a drip stream.

The present invention will be further understood from the drawings and the following detailed description.

DESCRIPTION OF PREFERRED EMBODIMENTS

Figure 1:
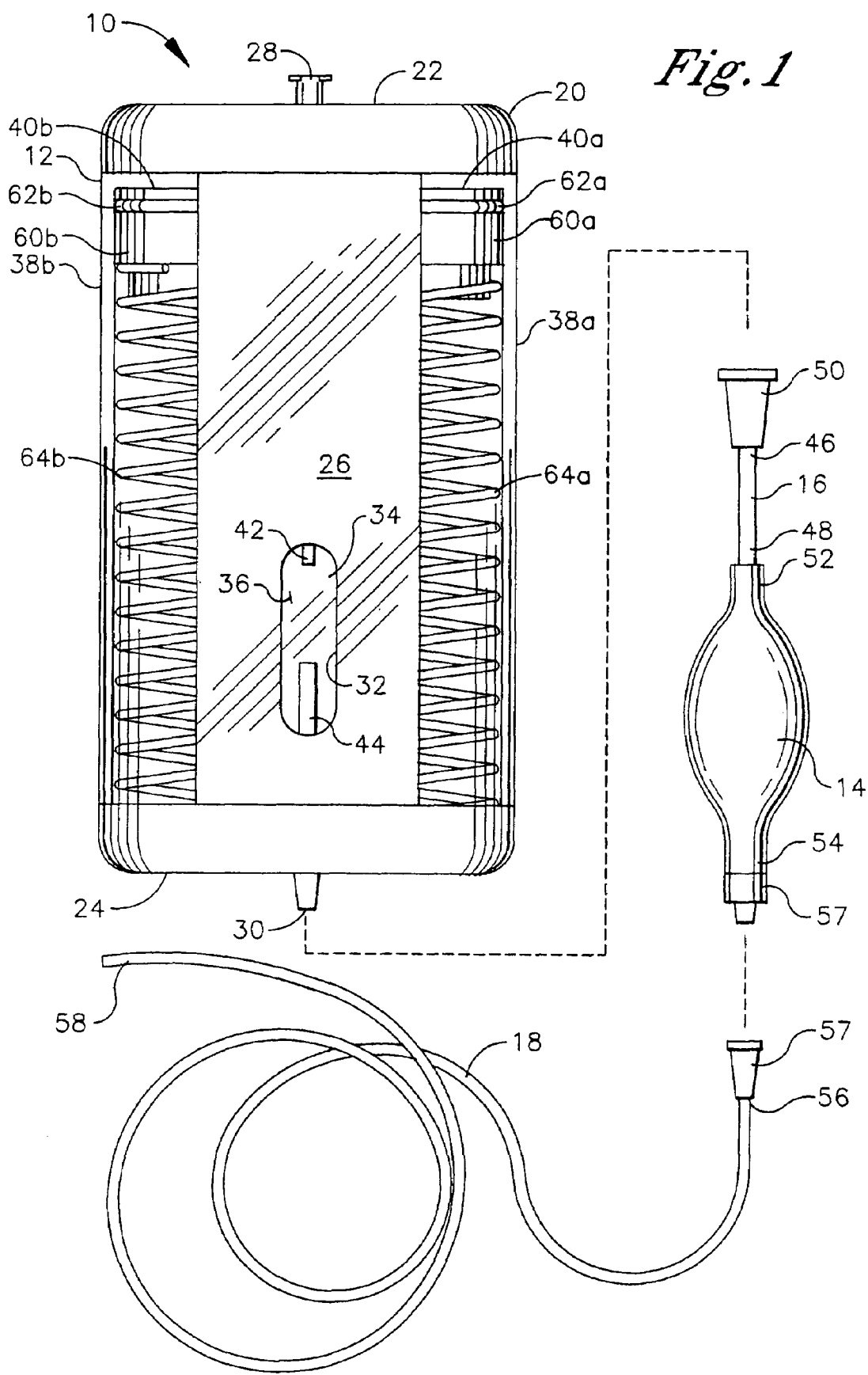
FIG. 1 is an elevational view of a medication delivery system of the present invention in a partially disassembled inactive state.

Referring to FIG. 1, a medication delivery system of the present invention is shown and generally designated 10. The medication delivery system 10 comprises an infusion pump 12 and a bolus injector 14. The medication delivery system 10 further comprises a connective tube 16, which provides fluid communication between the infusion pump 12 and the bolus injector 14, and a catheter 18, which provides fluid communication between the bolus injector 14 and a treatment site (not shown) in a user. The infusion pump 12 has a rigid opaque housing 20, which comprises a series of interconnected components. In particular, the housing 20 includes a top end cap 22, a bottom end cap 24 and a front face plate 26. The housing 20 inter alia functions as a structural frame and a protective shield for the remaining components of the infusion pump 12. The housing 20 is adapted to the external profile of the infusion pump 12, which is compactly sized for portability, enabling ready transport of the medication delivery system 10 by the user during normal daily activities. The housing 20 may be fitted with one or more optional accessories (not shown), which facilitate transport of the medication delivery system 10 by the user. For example, the housing 20 may be fitted with an external strap for wearing the pump 12 on the body of the user or the housing 20 may be fitted with an external clip for clipping the housing 20 to an article of clothing worn by the user, such as a trouser waistband or a belt.

A pump inlet port 28 extends through the top end cap 22 of the housing 20 and a pump outlet port 30 correspondingly extends through the bottom end cap 24 of the housing 20. The front face plate 26 is provided with an opening 32, which exposes a discharge sight window 34. The discharge sight window 34 is a light transmissive window, i.e., a transparent or translucent window, fitted into, or integral with, the surrounding wall of a drip chamber 36 enclosed within the housing 20 and described in greater detail below. The front face plate 26 is also configured to expose first and second storage sight windows 38a, 38b. The first storage sight window 38a is a light transmissive window fitted into, or integral with, the surrounding wall of a first medication storage chamber 40a retained by the housing 20. The second storage sight window 38b is similarly a light transmissive window fitted into, or integral with, the surrounding wall of a second medication storage chamber 40b retained by the housing 20. The discharge sight window 34, in cooperation with the opening 32, renders the interior of the drip chamber 36 visible to the user. The drip chamber 36 contains a drip tube 42 and a chamber outlet tube 44, which are described in greater detail below. The first and second storage sight windows 38a, 38b render the interiors of the first and second medication storage chambers 40a, 40b, respectively, visible to the user. An overlay (not shown) in the form of a paper or plastic sticker or the like, which displays a gradient of fluid level markings, may optionally be positioned adjacent to each storage sight window 38a, 38b to facilitate measurement of the fluid levels in the first and second medication storage chambers 40a, 40b without preventing the user from viewing the interiors of the first and second medication storage chambers 40a, 40b.

The connective tube 16 is a flexible transparent tube, which has an inside diameter, for example, of about 0.060 inches. The connective tube 16 has an inlet end 46 and an outlet end 48, wherein the inlet end 46 is removably coupled with the pump outlet port 30 by means of a conventional tube/port coupling 50, such as male and female Luer lock fittings. The bolus injector 14 is a fluid-tight flexible bladder, which has an injector inlet port 52 and an injector outlet port 54. The bolus injector 14 is formed from a flexible, preferably transparent, material, which renders the bolus injector 14 manually compressible when a fluid is contained therein. The bolus injector 14 typically has a fluid capacity in a range of about 4 to 6 ml. In accordance with the embodiment shown in FIG. 1, the bolus injector is an elastomeric squeeze bulb having an elastic memory, which returns the squeeze bulb to its original shape after deformation. Although not shown, a plastic bag or the like is an alternate bolus injector within the scope of the present invention. The alternate bolus injector is likewise flexible, but not substantially elastic.

The injector inlet port 52 of the bolus injector 14 is integrally connected with the outlet end 48 of the connective tube 16 in a substantially fixed manner and the injector outlet port 54 is removably coupled with an inlet end 56 of the catheter 18 by means of a conventional tube/port coupling 57, such as male and female Luer lock fittings. The catheter 18 is a flexible transparent tube preferably having an inside diameter substantially less than the inside diameter of the connective tube 16. For example, the inside diameter of the catheter 18 is about 0.025 inches. The catheter 18 has an outlet end 58, which is open to enable fluid flow therethrough. As noted above, the infusion pump 12 is designed to be worn by the user or otherwise connectively supported by the user. The bolus injector 14, however, is preferably freely suspended from the outlet end 48 of the connective tube 16 with the inlet end 46 of the connective tube 16 connected to the infusion pump 12.

The first and second medication storage chambers 40a, 40b are retained in parallel relation to one another by the top and bottom end caps 22, 24, which are fastened to the first and second medication storage chambers 40a, 40b by top retention screws 59 (shown in FIG. 2) and bottom retention screws (not shown), respectively. The first medication storage chamber 40a has a first piston, seal and spring set 60a, 62a, 64a positioned therein and the second medication storage chamber 40b has a corresponding second piston, seal and spring set 60b, 62b, 64b positioned therein. The first piston, seal and spring set 60a, 62a, 64a and second piston, seal and spring set 60b, 62b, 64b are substantially identical to one another. Accordingly, the following description of the first piston, seal and spring set 60a, 62a, 64a applies equally to the second piston, seal and spring set 60b, 62b, 64b. The first piston 60a is cooperatively configured so that the first piston 60a is slidably displaceable up and down within the first medication storage chamber 40a in response to expansion or compression of the first spring 64a as described below with respect to operation of the system 10. The first piston 60a has an outside diameter slightly less than the inside diameter of the first medication storage chamber 40a and the first seal 62a is an elastomeric O-ring positioned around the first piston 60a to maintain a fluid-tight seal between the wall of the first medication storage chamber 40a and the first piston 60a. The first spring 64a is a coiled metal spring fitted in the first medication storage chamber 40a and has an outside diameter less than the inside diameter of the first medication storage chamber 40a. The top end of the first spring 64a engages the first piston 60a and the bottom end of the first spring 64a engages the bottom of the first medication storage chamber 40a, which is integral with the vented bottom end cap 24.

Figure 2:
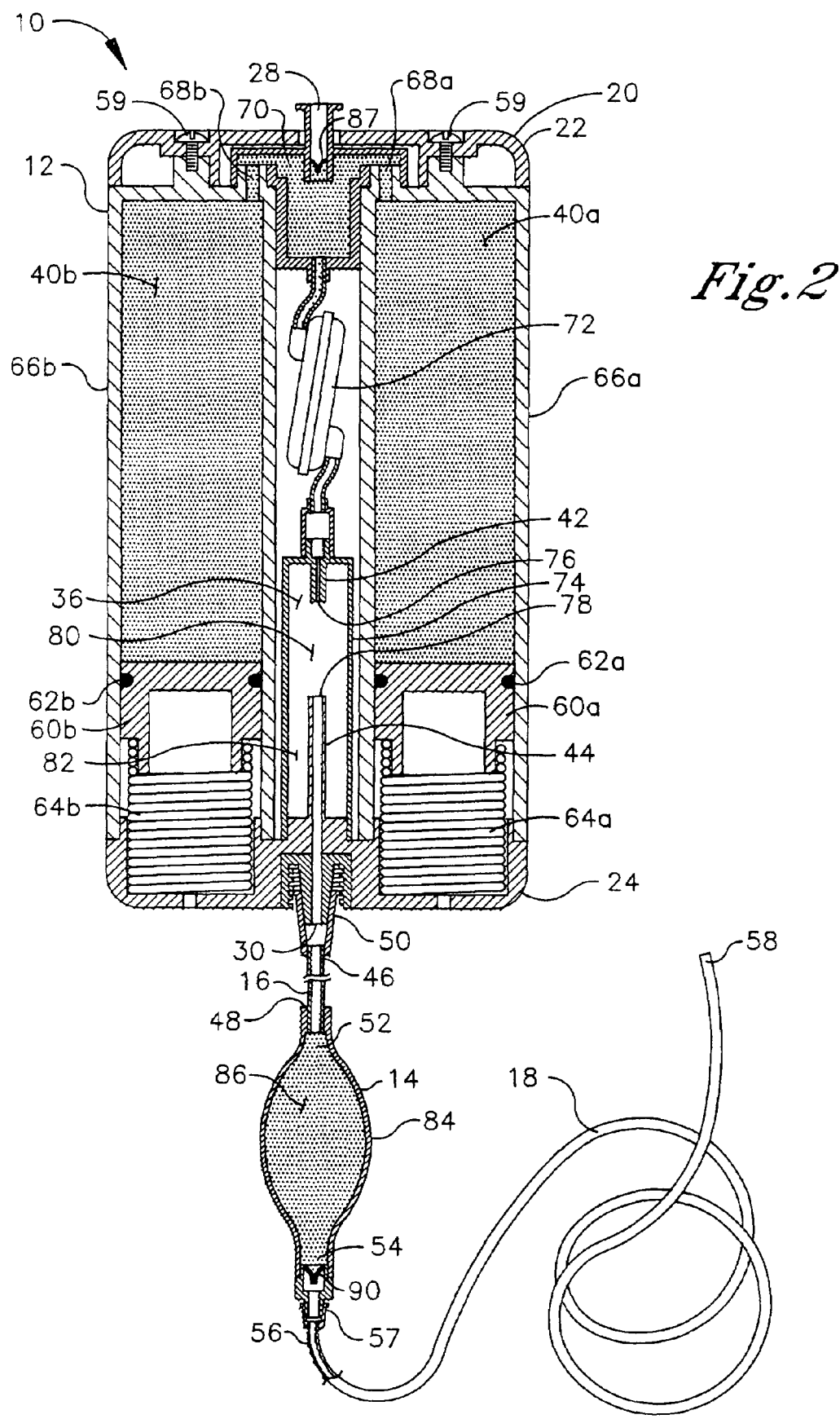
FIG. 2 is an elevational view of the medication delivery system of FIG. 1 in an active state immediately after charging the system with a fluid medication, wherein the infusion pump and bolus injector are shown in sectional.

Further details of the medication delivery system 10 are described below with reference to FIG. 2. The first and second medication storage chambers 40a, 40b have first and second tubular walls 66a, 66b, respectively. The first and second medication storage chambers 40a, 40b are substantially identically configured and each has a fluid capacity several times greater than the fluid capacity of the bolus injector 14. For example, each of the medication storage chambers 40a, 40b may have a fluid capacity of about 50 ml for a combined fluid capacity of about 100 ml. A first storage chamber outlet 68a is positioned at the top of the first medication storage chamber 40a and a second storage chamber outlet 68b is likewise positioned at the top of the second medication storage chamber 40b. The first and second storage chamber outlets 68a, 68b open into a manifold 70 which functions as a receiving chamber for the first and second storage chamber outlets 68a, 68b. A filter 72 is positioned in series downstream of the manifold 70. The filter 72 is a conventional in-line fluid filter which is designed to trap solid particles exceeding an appropriate maximum size, such as 2 microns, and prevent such particles from continuing downstream of the filter 72.

The filter 72 discharges into the drip tube 42 positioned in the drip chamber 36. The drip chamber 36 has a tubular wall 74 of substantially uniform inside diameter along its entire length and an inside diameter substantially greater than each of the outside diameters of the drip tube 42 and chamber outlet tube 44. The drip tube 42 functions as a flow restriction, having a substantially uniform inside diameter, which is significantly less than the inside diameter of the connective tube 16 or catheter 18. For example, the inside diameter of the drip tube 42 is about 0.002 inches. The drip tube 42 has an outlet end 76, which extends downwardly into the drip chamber 36 from the top of the drip chamber 36. The chamber outlet tube 44 has an inlet end 78, which correspondingly extends upwardly into the drip chamber 36 from the bottom of the drip chamber 36. The chamber outlet tube 44 has a substantially uniform inside diameter, which significantly is greater than the inside diameter of the drip tube 42. For example, the inside diameter of the chamber outlet tube is about 0.060 inches. A drip gap 80, which is a void space on the order of about 0.5 inches or more in length, is provided between the outlet end 76 of the drip tube 42 and the inlet end 78 of the chamber outlet tube 44. The drip gap 80 is aligned with the discharge sight window 34 and opening 32 (shown in FIG. 1) so that the drip gap 80 is visible to the user. Upward extension of the inlet end 78 of chamber outlet tube 44 into the bottom of the drip chamber 36 defines a fluid accumulation annulus 82 between the wall 74 of the drip chamber 36 and the chamber outlet tube 44.

The bolus injector 14, which in the present embodiment is a squeeze bulb, has a flexible wall 84 enclosing a bolus chamber 86. The flexible wall 84 is formed from an elastomeric material, which is capable of deformation when a sufficient displacement force is applied to it, but has an elastic memory, which returns the wall 84 to its original configuration after the displacement force causing the deformation is removed. When the wall 84 is not compressed to the point of deformation, the internal volume of the bolus chamber 86 is equal to the above-recited fluid capacity of the bolus injector 14, i.e., in a range of about 4 to 6 ml. When the wall 84 is compressed past the point of deformation, the internal volume of the bolus chamber 86 correspondingly decreases.

For purposes of illustrating its operation, the above-described system 10 is characterized in terms of three functionally distinct sub-assemblies, i.e., a system flowpath, a pair of automated fluid drive mechanisms and a manual fluid drive mechanism. The system flowpath is an essentially passive or static sub-assembly, whereas the automated and manual fluid drive mechanisms are essentially active or dynamic sub-assemblies. The system flowpath comprises in series the manifold 70, filter 72, drip tube 42, drip chamber 36, chamber outlet tube 44, connective tube 16, bolus chamber 86, and catheter 18. The two automated fluid drive mechanisms comprise in parallel the first piston, seal and spring set 60a, 62a, 64a and the second piston, seal and spring set 60b, 62b, 64b, respectively. The manual fluid drive mechanism comprises the flexible wall 84 of the bolus injector 14.

FIG. 1 shows the medication delivery system 10 in an inactive or passive state, wherein the inlet end 46 of the connective tube 16 is uncoupled from the pump outlet port 30 and the inlet end 56 of the catheter 18 is uncoupled from the injector outlet port 54. When the automated fluid drive mechanisms are in the inactive state, the first and second medication storage chambers 40a, 40b are substantially devoid of any fluid medication. Operation of the system 10 is initiated with a start-up procedure, wherein the medication delivery system 10 is charged with a desired fluid medication, such as a pain care medication.

The start-up procedure comprises placing the outlet end 58 of the catheter 18 in the treatment site, which is typically a surgical wound site. Placement of the outlet end 58 in the treatment site is effected by any conventional technique. A preferred technique for placing a catheter in a surgical wound site is described in U.S. Pat. No. 6,270,481, which is incorporated herein by reference. In accordance with this technique, a concentrically fitted introducer needle and insertion catheter (not shown) are simultaneously pierced through the outer surface of the skin adjacent to the surgical wound site and pushed through the skin until they enter the wound. The introducer needle is then removed while the insertion catheter remains in place. The outlet end 58 of the catheter 18 is threaded from the outer surface of the skin through insertion catheter into the wound. Finally, the insertion catheter is removed leaving the catheter 18 in place with the outlet end 58 in the wound and the remainder of the catheter 18 extending out through the skin.

The start-up procedure continues by coupling the inlet end 56 of the catheter 18 with the injector outlet port 54 by means of the tube/port coupling 57. The bolus injector 14 is primed with the fluid medication by injecting the fluid medication into the inlet end 46 of the connective tube 16 until the connective tube 16, bolus chamber 86 and catheter 18 are charged, preferably at or near their fluid capacity, with the fluid medication. Although the sequential order of the above-recited steps is preferred, the present invention is not so limited and alternate sequences of these steps are within the scope of the present invention.

The start-up procedure further comprises placing a charge of the fluid medication in the first and second medication storage chambers 40a, 40b. The volume of the charge typically approximates the total combined capacity of the chambers 40a, 40b and manifold 70, although the volume of the charge may alternatively be less than the total capacity of the chambers 40a, 40b and manifold 70, if desired. Placement of the fluid medication in the first and second medication storage chambers 40a, 40b is effected by injecting the fluid medication through the pump inlet port 28 using an injection means (not shown) such as a syringe or the like. The injection means discharges the fluid medication into the pump inlet port 28 at a pressure, which causes the fluid medication to urge open an inlet valve 87, which is a one-way check valve positioned at the pump inlet port 28. The inlet valve 87 is normally biased closed when fluid medication is not being injected into the pump inlet port 28.

The open inlet valve 87 enables the fluid medication to pass through the pump inlet port 28 into the manifold 70. The bulk of the charge is displaced under the pressure of the injection means from the manifold 70 through the first and second storage chamber outlets 68a, 68b into the first and second medication storage chambers 40a, 40b, respectively. The remainder of the charge remains in the manifold 70 or is diverted from the manifold 70 into the filter 72 under the pressure of the injection means. However, this remainder is very small relative to the bulk of the charge because the flow resistance into the filter 72 is substantially greater than the flow resistance into the first and second medication storage chambers 40a, 40b. Once the first and second medication storage chambers 40a, 40b are charged with the fluid medication, the inlet valve 87 closes and the injection means is withdrawn from the pump inlet port 28. The inlet end 46 of the connective tube 16 is then coupled with the pump outlet port 30 by means of the tube/port coupling 50.

Operation of the automated fluid drive mechanisms in cooperation with the first and second medication storage chambers 40a, 40b is described hereafter with respect to the first piston, seal and spring set 60a, 62a, 64a and first medication storage chamber 40a, it being understood that the description applies equally to the second piston, seal and spring set 60b, 62b, 64b and second medication storage chamber 40b, which are substantially identical to the first. The first medication storage chamber 40a has a volume which varies as a function of the position of the first piston 60a relative to the fixed wall 66a of the first medication storage chamber 40a. When the automated fluid drive mechanism is in the inactive state, the first medication storage chamber 40a is at its minimum volume, typically at or approaching zero. At this point the first spring 64a is expanded to a substantially more relaxed or less stressed position and the first piston 60a is in an extended upward position. When the automated fluid drive mechanism transitions to the active state as shown in FIG. 2, the first medication storage chamber 40a is at its charge volume, which typically exceeds the minimum volume of the first medication storage chamber 40a by slightly less than one-half the total volume of the charge of fluid medication to the system 10, the remainder of the total volume going to the second medication chamber 40b and the manifold 70. At this point the first spring 64a is compressed to a substantially more stressed or less relaxed position and the first piston 60a is in a depressed downward position.

The compressed first spring 64a exerts an upward expansion or displacement force on the first piston 60a when the automated fluid drive mechanism is in the active state, which biases the first piston 60a toward its extended upward position. Consequently, the displacement force of the first spring 64a against the first piston 60a in cooperation with the first seal 62a displaces the fluid medication from the first medication storage chamber 40a back through the first storage chamber outlet 68a in an automated manner, which requires no user intervention or additional driving force. The second piston, seal and spring set 60b, 62b, 64b likewise displace the fluid medication from the second medication storage chamber 40b back through the second storage chamber outlet 68b in the same manner. The pressure created by the automated fluid drive mechanisms directs displacement of the fluid medication past the closed inlet valve 87 at the pump inlet port 28 through the manifold 70 into the filter 72.

Figure 3:
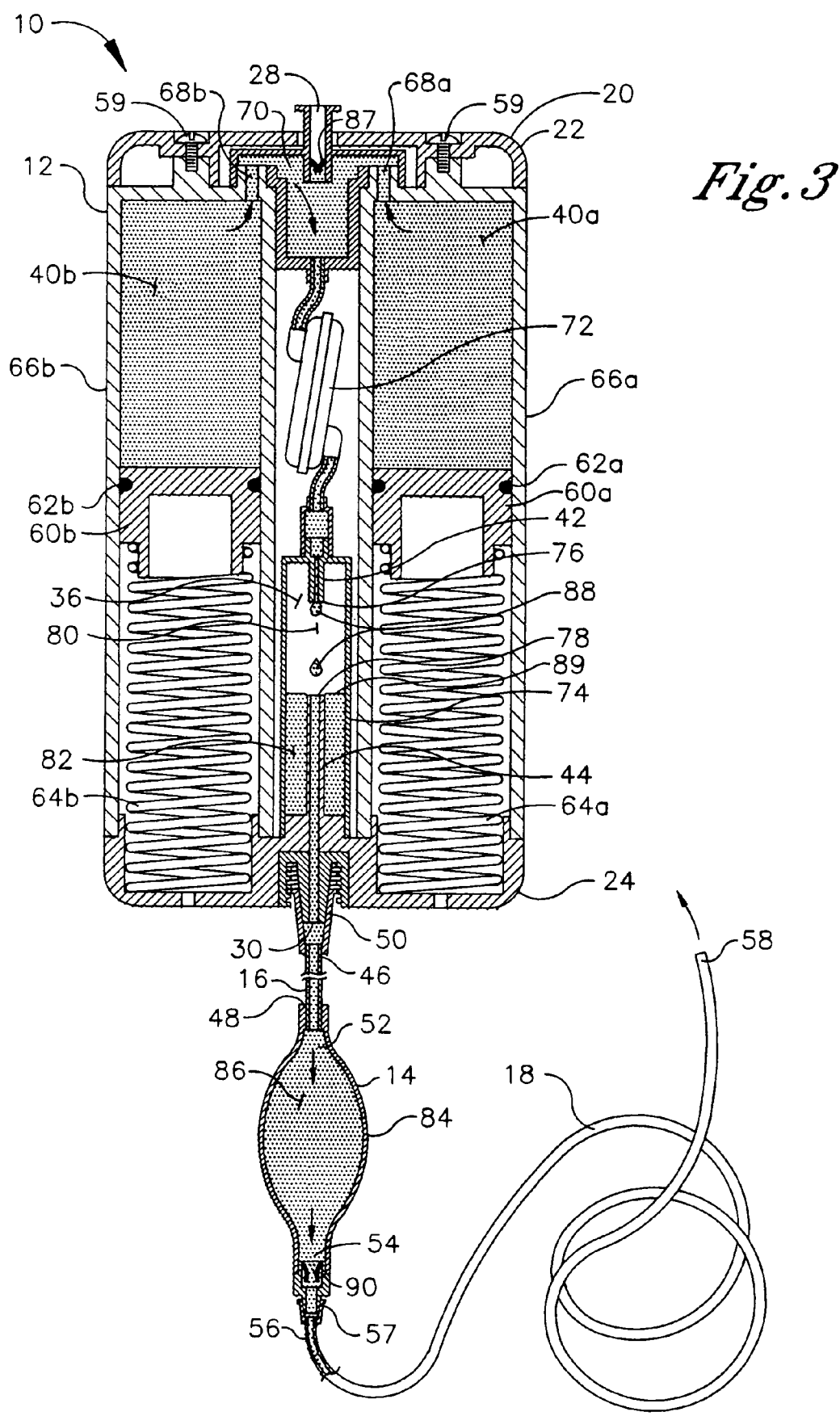
FIG. 3 is an elevational view of the medication delivery system of FIG. 1 during a an essentially steady-state automated mode of operation, wherein the infusion pump and bolus injector are shown in sectional.

With reference to FIG. 3, displacement of the fluid medication from the first and second medication storage chambers 40a, 40b through the manifold 70 and filter 72 by means of the automated fluid drive mechanisms creates a substantially continuous uninterrupted stream of fluid medication in this portion of the system flowpath. However, the relatively small inside diameter of the drip tube 42 creates a flow restriction of sufficient degree to convert the continuous steam of fluid medication to a discontinuous drip stream at the outlet end 76 of the drip tube 42. The drip tube 42 preferably has a smaller inside diameter than any other components of the system flowpath. Thus, the fluid medication is discharged from the outlet end 76 of the drip tube 42 downward into the drip gap 80 within the drip chamber 36 as a periodic series of droplets 88. Although the inlet end 78 of the chamber outlet tube 44 is aligned with the outlet end 76 of the drip tube 42, the bulk of the droplets 88 in the drip stream falling through the drip gap 80 are deflected into the fluid accumulation annulus 82 upon impact with the inlet end 78 rather than flowing into the chamber outlet tube 44.

When a sufficient volume of droplets 88 accumulate in the annulus 82 to fill the annulus 82, the fluid level 89 in the annulus 82 reaches the inlet end 78 of the chamber outlet tube 44. Ultimately the fluid medication spills over the inlet end 78 and continues through the chamber outlet tube 44 along the system flowpath into the injector inlet port 52. The fluid medication spillover into the chamber outlet tube 44 is substantially continuous, thereby converting the discontinuous drip stream back to a continuous stream in the chamber outlet tube 44. The ambient pressure of the fluid medication in the system flowpath urges open an outlet valve 90 positioned at the injector outlet port 54. The outlet valve is a one-way check valve, which is biased closed in the absence of the fluid medication. The ambient pressure of the fluid medication contacting the outlet valve 90 alone is sufficient to overcome the biasing force of the outlet valve 90 without reliance on any other external forces.

The open outlet valve 90 enables the fluid medication to exit the bolus chamber 86 via the injector outlet port 54 and flow as a substantially continuous stream of an extended dosage through the catheter 18 and out the outlet end 58 to the treatment site in an essentially steady-state manner. Delivery of the extended dosage of the fluid medication to the treatment site is characterized by a relatively moderate first flow rate over a relatively long time, for example, about 2 ml per hour over about 2 days.

The above-described operating mode of the system 10 shown in FIG. 3 is termed an automated or extended mode insofar as the system 10 operates in this mode by default without any need of user intervention once the fluid medication is charged to the system 10. In the absence of user intervention, the system 10 maintains the automated mode of operation in the essentially steady-state manner until substantially all of the fluid medication is displaced from the first and second medication storage chambers 40*a*, 40*b* or until the springs 64*a*, 64*b* reach their expansion limit, whichever occurs first. The automated mode of operation is deemed essentially steady-state because the system 10 discharges an extended substantially continuous stream of fluid medication to the treatment site at a relatively constant first flow rate for the duration of the automated mode of operation. An exemplary first flow rate of fluid medication from the system 10 is in a range of about 2 to 5 ml per hour.

The term "essentially steady-state" as used herein encompasses operating conditions, wherein the automated mode is not precisely steady-state due to relatively small fluctuations or perturbations, which may occur in the first flow rate of the fluid medication or which may occur in the continuity of the stream of fluid medication from the system 10. For example, if the frictional forces between the first and second walls 66*a*, 66*b* and the first and second pistons 60*a*, 60*b* and seals 62*a*, 62*b* remain constant while the displacement forces of the springs 64*a*, 64*b* decline with time throughout the automated mode, the first flow rate of the fluid medication from the system 10 may exhibit a relatively small correspondent decline with time. An exemplary decline rate of the flow rate under such conditions is relatively small, e.g., on the order of about 1% per hour.

An advantageous feature of the present system 10 is the passive conversion by the system flowpath of a continuous fluid medication stream to a more visible drip stream within the drip chamber 36. As noted above, the discharge sight window 34, in cooperation with the opening 32, enables the user to observe the interior of the drip chamber 36. However, it would be difficult to detect the presence of a continuous fluid stream within the drip chamber 36 due to the absence of light contrast between the continuous stream and the drip chamber wall 74. The intermittent droplets 88 of the drip stream provide greater light contrast than a continuous stream, which enables the user to visually monitor whether fluid medication is flowing through the system 10 or not in a relatively simple manner without disrupting operation of the system 10. The first, and second storage sight windows 38*a*, 38*b* also advantageously enable the user to easily visually monitor the remaining level of fluid medication in the first and second medication storage chambers 40*a*, 40*b*.

Another advantageous feature of the present embodiment is the raised position of the inlet end 78 of the drip chamber outlet tube 44, which is approximately at the volumetric center of the drip chamber 36. If the infusion pump 12 is inadvertently overturned during user activity, the configuration of the inverted drip chamber 36 nevertheless maintains the ratio of air to liquid in the drip chamber 36 constant at about 1 to 1 by trapping an air pocket in the fluid accumulation annulus 82. Therefore, fluid medication cannot drain back into the drip chamber 36 via the chamber outlet tube 44 because it is unable to displace the air pocket out the inlet end 78. If the drip chamber 36 were not so configured, the entire drip chamber 36 could fill with fluid medication upon inversion and remain in the drip chamber 36 even after the drip chamber 36 is restored to its upright position. If the drip chamber 36 is filled in its entirety with fluid medication, the user is unable to visually detect fluid flow through the drip chamber 36.

Figure 4:
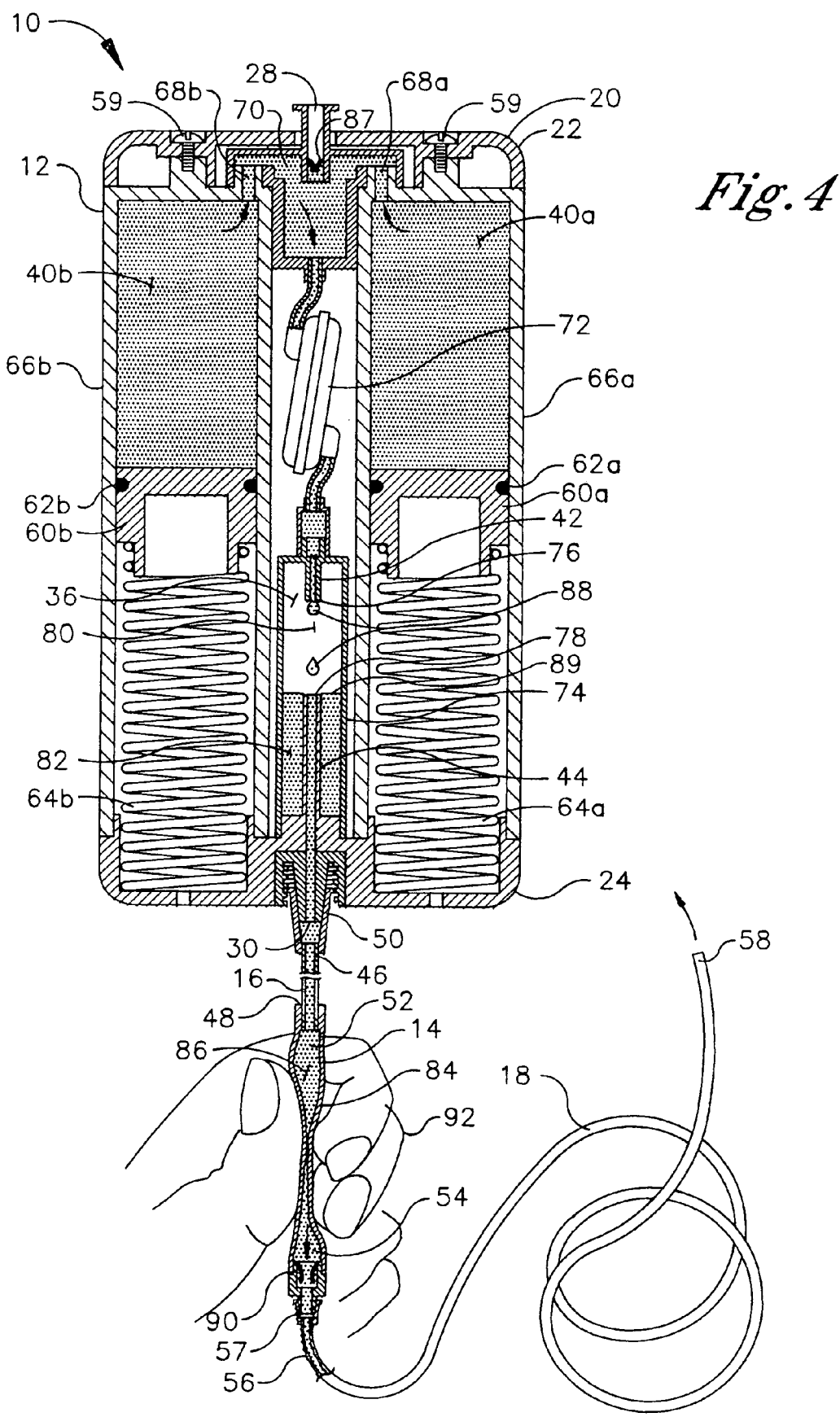
FIG. 4 is an elevational view of the medication delivery system of FIG. 1 during a manual mode of operation, wherein the infusion pump and bolus injector are shown in sectional.

The manual fluid drive mechanism is transitioned to an active state during an alternate mode of operation termed the manual or instantaneous mode, which is described below with reference to FIG. 4. The manual mode of operation enables the user to manually override the automated mode of operation and provide instantaneous delivery of a bolus dosage of the fluid medication to the treatment site when desired. The manual mode can be performed at any time when the bolus chamber 86 is charged with the fluid medication, and preferably when the bolus chamber 86 is charged at or near its fluid capacity. Operation in the manual mode is effected by manually applying a sufficient displacement force to the flexible wall 84 of the bolus injector 14 to deform the wall 84 and collapse the bolus chamber 86, which contains a volume of the fluid medication. The displacement force is typically applied by squeezing the wall 84 in the hand 92 of a user, e.g., between the thumb and fingers as shown. Collapse of the bolus chamber 86 applies a displacement force to the fluid medication therein, which maintains the outlet valve 90 at the injector outlet port 54 open and instantaneously drives substantially all of the fluid medication, or at least the bulk of the fluid medication, downstream from the bolus chamber 86 through the injector outlet port 54 and into the catheter 18. Essentially none, or relatively little, of the fluid medication residing in the bolus chamber 86 is driven upstream from the bolus chamber 86 when the displacement force is applied to the wall 84 because of the severe flow restriction provided by the drip chamber 36 and in particular, the drip tube 42.

The fluid medication manually driven from the bolus chamber 86 through the catheter 18 to the treatment site is termed the bolus dosage. In contrast to the extended dosage, delivery of the bolus dosage to the treatment site may generally be characterized by a relatively higher second flow rate over a relatively short time, for example, about 4 ml instantaneously. Thus, the bolus dosage is essentially delivered to the treatment site in a single large pulse. The volume of the fluid medication in the bolus dosage is preferably approximately equal to the fluid capacity of the bolus injector 14, i.e., in a range of about 4 to 6 ml.

Once the bolus dosage is delivered to the treatment site, the displacement force is withdrawn from the wall 84 and the outlet valve 90 at the injector outlet port 54 closes. The bolus chamber 86 begins recharging with the fluid medication from the first and second medication storage chambers 40*a*, 40*b* in accordance with the automated mode of operation if fluid medication is present in the medication storage chambers 40*a*, 40*b*. In addition to the displacement force applied to the system flowpath by the automated fluid drive mechanisms upstream of the bolus injector 14, which drives the fluid medication from the first and second medication storage chambers 40*a*, 40*b* into the bolus chamber 86, the elastic memory of the bolus injector 14 may apply a suction force to the system flowpath both upstream and downstream of the bolus injector 14. However, the closed outlet valve 90 at the injector outlet port 54 negates the downstream effect of the suction force, blocking the backflow of fluid into the bolus chamber 86 from the catheter 18 or treatment site. The drip chamber 36 negates the upstream effect of the suction force, preventing the bolus injector 14 from drawing the fluid medication into the bolus chamber 86 at a faster rate than is dictated by the drip tube 42.

When the bolus chamber 86 is recharged preferably at or near its fluid capacity, the ambient pressure of the fluid medication reopens the outlet valve 90 at the injector outlet port 54, enabling the fluid medication to resume flow as a substantially continuous stream to the treatment site. As is apparent from above, the drip chamber 36 limits the rate at which the bolus chamber 86 can recharge to substantially prevent a user from overmedicating oneself by attempting to repeat the manual mode of operation in a relatively short time period.

The medication delivery system 10 has been described above as comprising a single infusion pump 12 having two medication storage chambers 40a, 40b, respectively. However, the present invention is not so limited. It is readily apparent to the skilled artisan that the present invention additionally encompasses alternate embodiments of the medication delivery system 10, wherein the infusion pump has a single medication storage chamber or includes three or more medication storage chambers. Such alternate embodiments require only minor modifications of the present teaching in a manner within the purview of the skilled artisan. The first and second springs 64a, 64b have also been described in the embodiment of the invention set forth above as being identical. The present invention additionally encompasses alternate embodiments of the medication delivery system 10, wherein the first spring 64a has a different displacement force than the second spring 64b. For example, the first spring 64a could be selected with a displacement force substantially greater than the displacement force of the second spring 64b so that all or some of the fluid medication would be discharged from the first medication storage chamber 40a before any fluid medication would be discharged from the second medication storage chamber 40b. If there is a decline in the fluid flow rate from the system 10 during the automated mode as described above, the practitioner can alter the decline by selecting the first and second springs 64a, 64b with various balanced or unbalanced displacement forces as desired.

Figure 5:
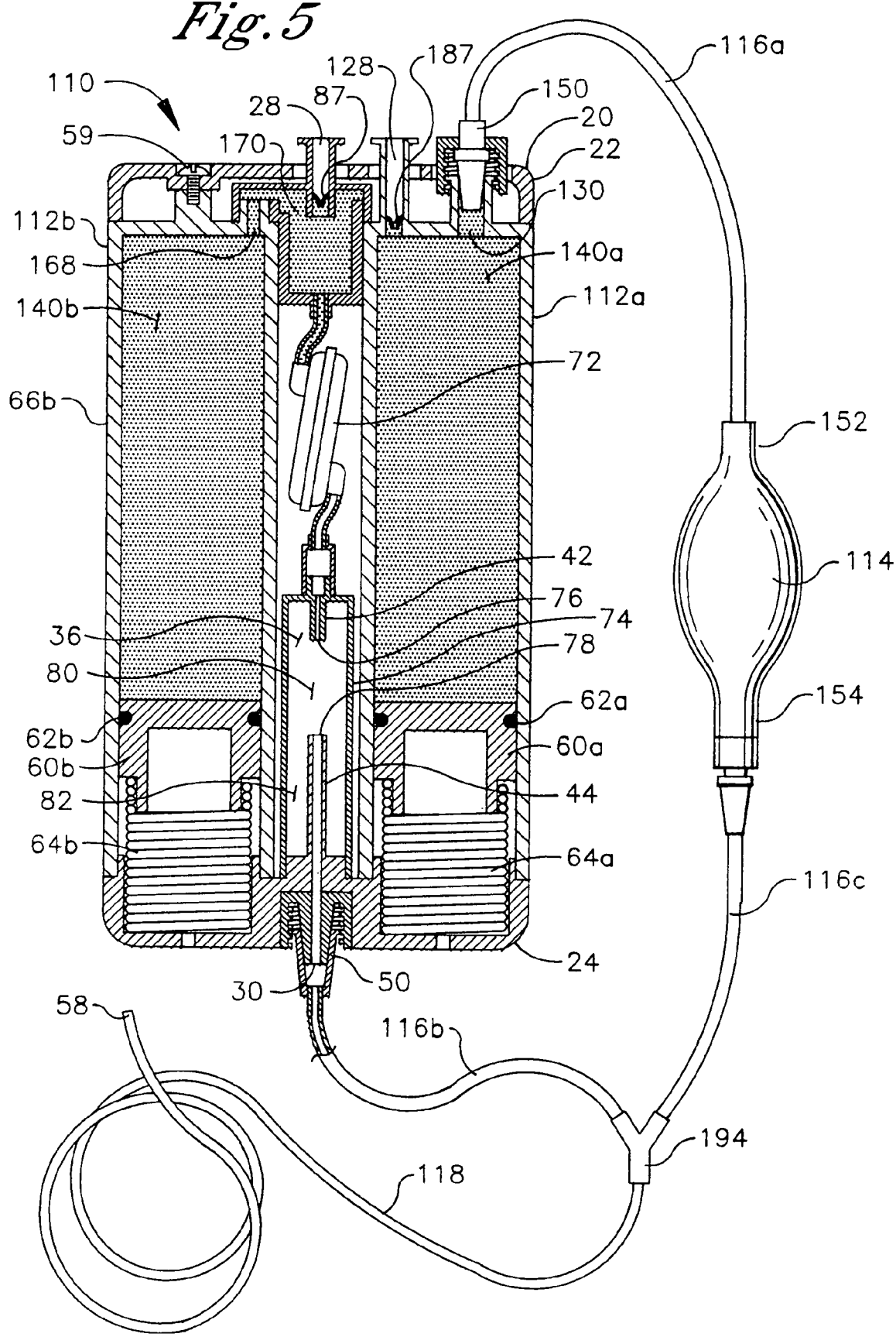
FIG. 5 is an elevational view of an alternate embodiment of the medication delivery system of the present invention in an active state immediately after charging the system with a fluid medication, wherein the infusion pump is shown in sectional.

Referring to FIG. 5, an alternate embodiment of a medication delivery system of the present invention is shown and generally designated 110. The present medication delivery system 110 differs somewhat from the medication delivery system 10 described above. The medication delivery system 10 described above employs a single infusion pump 12 having two medication storage chambers 40a, 40b and two automated fluid drive mechanisms. The medication storage chambers 40a, 40b of the medication delivery system 10 are in fluid communication with one another via a single flowpath upstream of the bolus injector 14. Thus, the infusion pump 12 in cooperation with the bolus injector 14 serves both the automated and manual modes of system operation. In contrast, the medication delivery system 110 of the present embodiment employs separate first and second infusion pumps 112a, 112b, which are in fluid isolation from one another because each has a separate flowpath upstream of a bolus injector 114. The first infusion pump 112a has a first medication storage chamber 140a, which serves the manual mode of system operation exclusively, while the second infusion pump 112b has a second medication storage chamber 140b, storage chamber outlet 168b, and manifold 170, which serve the automated mode of system operation exclusively. The remainder of the flowpath of the second infusion pump 112b is substantially similar to that described in the medication delivery system 10. Accordingly, the elements of FIG. 5, which are common to FIGS. 1-4, are denoted by the same reference characters.

The primary functional difference between the system 110 and the system 10 is that the automated and manual modes of the system 110 operate independently in parallel, whereas the automated and manual modes of the system 10 operate cooperatively in series. To enable independent operation of the system 110, the first medication storage chamber 140a is provided with a separate inlet port 128 having an one-way inlet valve 187, an outlet port 130 and a tube/port coupling 150, which are similar to the corresponding elements employed in the second medication storage chamber 140b. However, the outlet port 130 has a flow restriction (not shown) positioned therein to regulate the fluid flow rate therethrough and to substantially prevent backflow. An injector inlet tube 116a connects the first medication storage chamber 140a with the bolus injector 114 via the outlet port 130 and the injector inlet port 152. An injector outlet tube 116b connects the bolus injector 114 with a "Y" fitting junction 194 via the injector outlet port 154. It is noted that the outlet valve (not shown) positioned at the injector outlet port 154 has a stronger pressure rating than that of the system 10 so that it only opens in response to a displacement force on the bolus injector 114. A connective tube 116c connects the second infusion pump 112b with the "Y" fitting junction 194 via the pump outlet port 30. The tubes 116b and 116c are joined at the "Y" fitting junction 194 and a common flow tube 118, preferably a catheter, exits the "Y" fitting junction 194 to a treatment site. One apparent advantage of the present system 110 is that different fluid medications can be stored in each of the medication storage chambers 140a, 140b and independently delivered to the treatment site.

The medication delivery system 110 has been described above as having a single medication storage chamber 140a or 140b for each infusion pump 112a or 112b, respectively. However, the present invention is not so limited. It is readily apparent to the skilled artisan that the present invention additionally encompasses alternate embodiments of the medication delivery system 110, wherein the infusion pump includes two or more medication storage chambers. Such alternate embodiments require only minor modifications of the present teaching in a manner within the purview of the skilled artisan.

Figure 6:
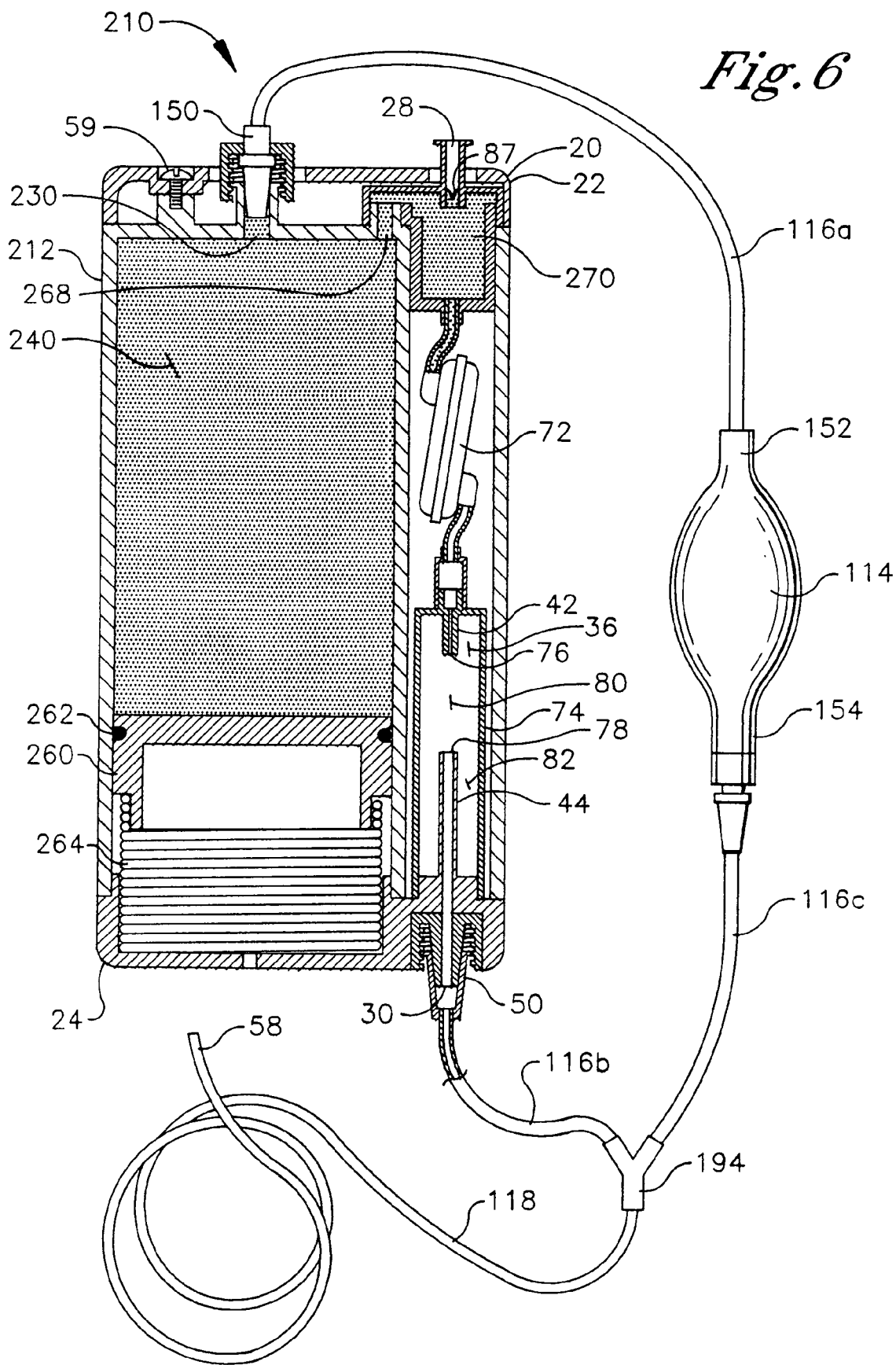
FIG. 6 is an elevational view of another alternate embodiment of the medication delivery system of the present invention in an active state immediately after charging the system with a fluid medication, wherein the infusion pump is shown in sectional.

Referring to FIG. 6, another alternate embodiment of a medication delivery system of the present invention is shown and generally designated 210. The medication delivery system 210 employs a single infusion pump 212 having a single medication storage chamber 240, piston, seal and spring set 260, 262, 264, storage chamber outlet 268, and manifold 270. The automated and manual modes of operation are served by the same infusion pump 212, but via separate flowpaths. To enable separate flowpaths, an outlet port 230 is positioned in the top of the medication storage chamber 240. In all other respects the medication delivery system 210 is substantially the same as the medication delivery system 110. Accordingly, the elements of FIG. 6, which are common to FIG. 5, are denoted by the same reference characters.

While the forgoing preferred embodiments of the invention have been described and shown, it is understood that alternatives and modifications, such as those suggested and others, may be made thereto and fall within the scope of the invention.

I claim:

1. A method for delivering a fluid medication to a treatment site of a patient comprising:

displacing a liquid fluid medication in an initial continuous stream from a fluid storage chamber to a pump flowpath by transitioning an elastic member from a more stressed position to a less stressed position, said pump flowpath including a flow restriction, a drip chamber, and an outlet tube, wherein said drip chamber has a drip chamber sidewall, an upper portion, and a lower portion, said flow restriction exiting into said drip chamber and said outlet tube positioned beneath said flow restriction in said lower portion separated from said flow restriction by a drip gap, wherein said outlet tube has an extension segment with an inlet opening and a smaller cross section than said drip chamber, said extension segment extending into said drip chamber through said lower portion toward said upper portion to define an annular fluid accumulation space between said outlet tube and said drip chamber sidewall in said lower portion, thereby segmenting said drip chamber into said fluid accumulation space and a remainder space;

converting said initial continuous stream of said fluid medication to a drip stream in said flow restriction;

accumulating at least some of said fluid medication exiting said flow restriction in said fluid accumulation space, while maintaining an air pocket in said remainder space to define an air-liquid interface between said fluid accumulation space and said remainder space;

spilling said fluid medication in said fluid accumulation space in an essentially continuous steady-state manner over an edge of said inlet opening of said extension segment extending into said drip chamber and fixed at said air-liquid interface, thereby reverting said drip stream to a reverted continuous stream in said outlet tube; and conveying said reverted continuous stream of said fluid medication from said outlet tube to a downstream treatment site of a patient.

2. The method of claim 1, wherein said a flow restriction is sized to convert said initial continuous stream of fluid medication to said drip stream.

3. The method of claim 1, wherein said pump flowpath includes a sight window oriented to enable visual contact with said drip chamber.

4. The method of claim 1 further comprising conveying said fluid medication from said fluid storage chamber to a bolus chamber and discharging said fluid medication in an instantaneous mode from said bolus chamber to said downstream treatment site.

5. The method of claim 1 further comprising conveying said fluid medication from said fluid storage chamber to a bolus chamber and discharging said fluid medication in an essentially steady-state mode from said bolus chamber to said downstream treatment site.

6. A method for delivering a fluid medication to a treatment site of a patient comprising:

displacing a liquid fluid medication in an initial continuous stream from a fluid storage chamber to a pump flowpath by transitioning an elastic member from a more stressed position to a less stressed position, said pump flowpath including a flow restriction, a drip chamber, and an outlet tube, wherein said drip chamber has a drip chamber sidewall, an upper portion, and a lower portion, said flow restriction exiting into said drip chamber and said outlet tube positioned beneath said flow restriction in said lower portion separated from said flow restriction by a drip gap, wherein said outlet tube has an extension segment with an inlet opening and a smaller cross section than said drip chamber, said extension segment extending into said drip chamber through said lower portion toward said upper portion to define an annular fluid accumulation space between said outlet tube and said drip chamber sidewall in said lower portion, thereby segmenting said drip chamber into said fluid accumulation space and a remainder space;

converting said initial continuous stream of said fluid medication to a drip stream in said flow restriction;

accumulating at least some of said fluid medication exiting said flow restriction in said fluid accumulation space, while maintaining an air rocket in said remainder space to define an air-liquid interface between said fluid accumulation space and said remainder space;

spilling said fluid medication in said fluid accumulation space in an essentially continuous steady-state manner over an edge of said inlet opening of said extension segment extending into said drip chamber and fixed at said air-liquid interface, thereby reverting said drip stream to a reverted continuous stream in said outlet tube;

conveying said reverted continuous stream of said fluid medication from said outlet tube through a pump outlet to a bolus chamber; and discharging said reverted continuous stream of said fluid medication in an essentially steady-state mode or an instantaneous mode from said bolus chamber to a downstream treatment site of a patient.

7. The method of claim 6, wherein said flow restriction is sized to convert said initial continuous stream of fluid medication to said drip stream.

8. The method of claim 6, wherein said pump flowpath includes a sight window oriented to enable visual contact with said drip chamber.

9. A method for delivering a fluid medication to a treatment site of a patient comprising:

displacing a liquid fluid medication from a fluid storage chamber to a pump flowpath by transitioning an elastic member from a more stressed position to a less stressed position, said pump flowpath including a flow restriction, a drip chamber, and an outlet tube, wherein said drip chamber has a drip chamber sidewall, an upper portion, and a lower portion, said flow restriction exiting into said drip chamber and said outlet tube positioned beneath said flow restriction in said lower portion separated from said flow restriction by a drip gap, wherein said outlet tube has an extension segment with an inlet opening and a smaller cross section than said drip chamber, said extension segment extending into said drip chamber through said lower portion toward said upper portion to define an annular fluid accumulation space between said outlet tube and said drip chamber sidewall in said lower portion, thereby segmenting said drip chamber into said fluid accumulation space and a remainder space;

conveying said fluid medication through said drip chamber to a downstream treatment site of a patient by accumulating at least some of said fluid medication exiting said flow restriction in said fluid accumulation space while maintaining an air pocket in said remainder space to define an air-liquid interface between said fluid accumulation space and said remainder space and spilling said fluid medication in said fluid accumulation space in an essentially continuous steady-state manner over an edge of said inlet opening of said extension segment extending into said drip chamber and fixed at said air-liquid interface; and maintaining an essentially constant ratio of liquid to air in said drip chamber independent of the orientation of said drip chamber relative to the orientation of said fluid storage chamber.

10. The method of claim 9 further comprising converting said fluid medication from an initial continuous stream displaced from said fluid storage chamber to a drip stream in said flow restriction, wherein said fluid medication is conveyed through said drip chamber as said drip stream;

thereafter reverting said drip stream to a reverted continuous stream in said outlet tube; and conveying said fluid medication from said outlet tube to said downstream treatment site of a patient as said reverted continuous stream.

11. The method of claim 10, wherein said flow restriction is sized to convert said initial continuous stream of fluid medication to said drip stream.

12. The method of claim 9, wherein said fluid accumulation space determines said ratio of liquid to air in said drip chamber.

13. The method of claim 12, wherein air in said air pocket displaces said accumulated fluid medication from said fluid accumulation space when said drip chamber is inverted.

14. The method of claim 9 further comprising conveying said fluid medication from said fluid storage chamber to a bolus chamber and discharging said fluid medication in an instantaneous mode from said bolus chamber to said downstream treatment site.

15. The method of claim 9 further comprising conveying said fluid medication from said fluid storage chamber to a bolus chamber and discharging said fluid medication in an essentially steady-state mode from said bolus chamber to said downstream treatment site.

16. A method for delivering a fluid medication to a treatment site of a patient comprising:

displacing a first portion of a liquid fluid medication from a fluid storage chamber to a pump flowpath by transitioning an elastic member from a more stressed position to a less stressed position, said pump flowpath including a flow restriction, a drip chamber, and an outlet tube, wherein said drip chamber has a drip chamber sidewall, an upper portion, and a lower portion, said flow restriction exiting into said drip chamber and said outlet tube positioned beneath said flow restriction in said lower portion separated from said flow restriction by a drip gap, wherein said outlet tube has an extension segment with an inlet opening and a smaller cross section than said drip chamber, said extension segment extending into said drip chamber through said lower portion toward said upper portion to define an annular fluid accumulation space between said outlet tube and said drip chamber sidewall in said lower portion, thereby segmenting said drip chamber into said fluid accumulation space and a remainder space;

conveying said first portion of said fluid medication through said drip chamber while accumulating at least some of said first portion of said fluid medication exiting said flow restriction in said fluid accumulation space and maintaining an air pocket in said remainder space to define an air-liquid interface between said fluid accumulation space and said remainder space;

spilling said first portion of said fluid medication in said fluid accumulation space in an essentially continuous steady-state manner over an edge of said inlet opening of said extension segment extending into said drip chamber and fixed at said air-liquid interface, thereby discharging said first portion of said fluid medication from said drip chamber;

conveying a second portion of said fluid medication through a pump outlet to a bolus chamber;

discharging said second portion of said fluid medication from said bolus chamber to a downstream treatment site of a patient; and maintaining an essentially constant ratio of liquid to air in said drip chamber independent of the orientation of said drip chamber relative to the orientation of said fluid storage chamber.

17. The method of claim 16, wherein said fluid accumulation space determines said ratio of liquid to air in said drip chamber.

18. The method of claim 17, wherein air in said air pocket displaces said accumulated first portion of said fluid medication from said fluid accumulation space when said drip chamber is inverted.

* * * * *